United States Patent [19]

Drabek et al.

[11] 4,151,298
[45] Apr. 24, 1979

[54] ANTHELMINTIC COMPOSITIONS

[75] Inventors: Jozef Drabek, Oberwil; Alfred Meyer, Basel, both of Switzerland

[73] Assignee: Ciba-Geigy Corporation, Ardsley, N.Y.

[21] Appl. No.: 867,653

[22] Filed: Jan. 6, 1978

[30] Foreign Application Priority Data

Jan. 10, 1977 [CH] Switzerland .............................. 266/77
Dec. 7, 1977 [CH] Switzerland ........................ 15001/77

[51] Int. Cl.² ....................... A01N 9/20; C07C 121/78
[52] U.S. Cl. .................................. 424/304; 260/465 E
[58] Field of Search ...................... 260/465 E; 424/304

[56] References Cited

U.S. PATENT DOCUMENTS

| | | | |
|---|---|---|---|
| 3,551,573 | 12/1970 | Baber et al. ............................ | 424/304 |
| 3,702,861 | 11/1972 | Howe ................. | 260/465 E |
| 3,982,015 | 9/1976 | Drabek ................. | 424/304 |
| 4,000,314 | 12/1976 | Drabek ................. | 424/304 |

Primary Examiner—Dolph H. Torrence
Attorney, Agent, or Firm—Harry Falber

[57] ABSTRACT

This invention concerns anthelmintic compositions which contain as active component anilinomethylenemalononitrile derivatives corresponding to the formula

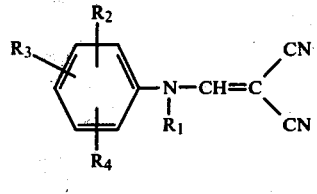

wherein $R_1$ represents hydrogen, $C_1$–$C_6$alkyl, the propargyl group or the benzyl radical, $R_2$ represents hydrogen, $C_1$–$C_4$alkyl, halogen, the trifluoromethyl group, the nitro group or the cyano group, $R_3$ represents hydrogen, halogen, the trifluoromethyl group or the nitro group, and $R_4$ represents hydrogen or halogen, with the proviso that $R_1$ may only be the propargyl group or the benzyl radical if at least one of the symbols $R_2$ or $R_3$ represents the trifluoromethyl group, and the use of the compositions for combating helminths in domestic animals and productive livestock.

4 Claims, No Drawings

ANTHELMINTIC COMPOSITIONS

The present invention relates to anthelmintic compositions which contain as active component anilinomethylenemalononitrile derivatives and to their use for combating heliminths, especially *Fasciola hepatica*, in domestic animals and productive livestock.

The active compounds have the general formula I

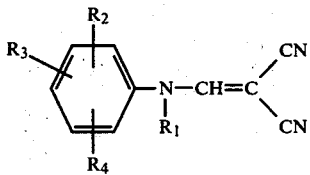

wherein
$R_1$ represents hydrogen, $C_1$–$C_6$alkyl, the propargyl group or the benzyl radical,
$R_2$ represents hydrogen, $C_1$–$C_4$alkyl, halogen, the trifluoromethyl group, the nitro group or the cyano group,
$R_3$ represents hydrogen, halogen, the trifluoromethyl group or the nitro group, and
$R_4$ represents hydrogen or halogen,
with the proviso that $R_1$ may only be the propargyl group or the benzyl radical if at least one of the symbols $R_2$ or $R_3$ represents the trifluoromethyl group.

Active compounds distinguished by a particularly outstanding anthelmintic action are those which fall under the following restricted formula Ia

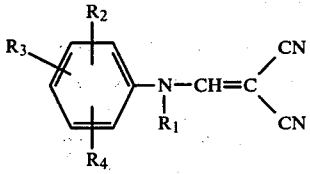

wherein
$R_1$ represents hydrogen, $C_1$–$C_6$alkyl, the propargyl group or the benzyl radical,
$R_2$ and $R_3$, each independently of the other, represent hydrogen, halogen, methyl, the trifluoromethyl group or the nitro group, and
$R_4$ represents hydrogen or halogen,
with the proviso that $R_1$ may only be the propargyl group or the benzyl radical if at least one of the symbols $R_2$ or $R_3$ represents the trifluoromethyl group.

Within the anthelmintic active compounds of the formula I referred to above, compounds which may be regarded as especially active against trematoda are those of the following restricted formula Ib

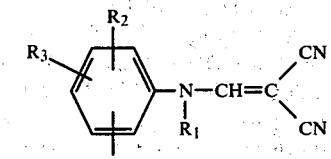

wherein
$R_1$ represents hydrogen, $C_1$–$C_6$alkyl, the propargyl group or the benzyl radical,
$R_2$ and $R_3$, each independently of the other, represent chlorine, methyl, the trifluoromethyl group or the nitro group, and
$R_4$ represents hydrogen or chlorine,
with the proviso that $R_1$ may only be the propargyl group or the benzyl radical if at least one of the symbols $R_2$ or $R_3$ represents the trifluoromethyl group.

The term "halogen" is to be understood as meaning, fluorine, chlorine, bromine and iodine.

The alkyl radicals can be straight-chain or branched. Examples of alkyl radicals are: methyl, ethyl, n-propyl, isopropyl, n-butyl, isobutyl, sec-butyl, tert-butyl, n-amyl, isoamyl and also the isomers of the hexyl radical.

The compounds of the formula I are known partly from U.S. Pat. No. 3,551,573 and partly from German Offenlegungsschrift Nos. 2,535,769 and 2,601,052, and are described in these publications as being active against insects which damage plants.

The compounds of the formula I are obtained by methods which are known per se and which are also performed in the publications referred to above. Accordingly, the compounds of the formula I which are both substituted and unsubstituted at the nitrogen atom of the aniline radical can be prepared by reaction of the suitable aniline compounds with ethoxymethylenemalononitrile. In addition, the compounds of the formula I which are substituted at the nitrogen atom of the aniline radical can be obtained by alkylation with dialkyl sulphate.

The following reaction schemes will illustrate the above methods of obtaining the compounds of the formula I:

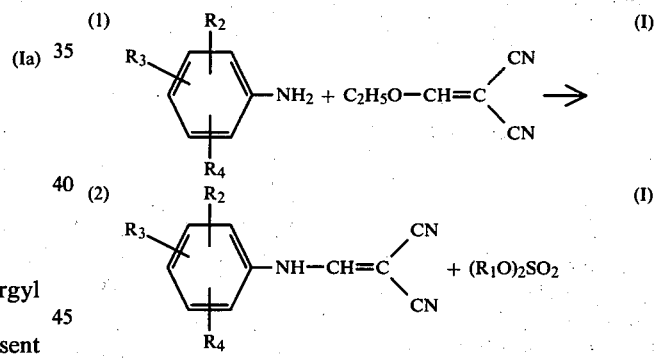

Among the endoparasites which occur in warm-blooded animals, the helminths especially cause great harm. Animals attacked by these parasites are not only retarded in their growth and exhibit a marked diminution in their useful performance, but are to some extent so severely harmed that they die. In order to prevent, or at least to reduce, losses in animal husbandry, which can be quite substantial if an outbreak of helminthiasis assumes epidemic proportions in livestock, unremitting efforts are being made to provide agents for combating helminths, including their development stages.

Accordingly, a large number of substances having anthelmintic action are known, but they are unable to satisfy the requirements made of them in the desired manner, because for example they do not have a sufficient potency when administered in well tolerated doses or they cause undesirable side-effects, such as toxaemia, when administered in therapeutic doses.

The anilinomethylenemalononitrile derivatives of the formula I are distinguished by good anthelmintic action against *nematoda, cestoda* and, especially, *trematoda*. In particular, their action against *fasciolida* (*Fasciola hepatatica*) is to be highlighted.

The following compound is especially preferred on account of its action against *fascioliasis*:

N-(2,2-dicyanovinyl)-N-2-methyl-4-nitro-5-chloroaniline.

EXAMPLE 1

Preparation of N-(2,2-dicyanovinyl)-2-chloro-5-trifluoromethylaniline 19.6 Parts of 2-chloro-5-trifluoromethyl-aniline and 12.2 parts of ethoxymethylenemalononitrile are dissolved in 125 parts of ethanol and the mixture is refluxed for 48 hours. After cooling, the precipitated product is collected by filtration and washed with ethanol. Recrystallisation from ethanol affords the above product with a melting point of 166°-169° C. and in a 70% yield.

EXAMPLE 2

Preparation of N-(2,2-dicyanovinyl)-N-ethyl-3,5-bis-trifluoromethyl-aniline 15.26 parts of 3,5-bis-trifluoromethylanilinomethylenemalononitrile together with 13.82 parts of potassium carbonate and 8.14 parts of diethyl sulphate are charged into 150 parts of tetrahydrofurane and the mixture is refluxed for 22 hours. After addition of water, the mixture is extracted with ether. The ether is evaporated off and the oily residue is precipitated as a solid by addition of hexane. The solid residue is crystallised from a mixture of methanol/water, yielding the above product with a melting point of 118°-120° C.

EXAMPLE 3

Preparation of N-(2,2-dicyanovinyl)-N-benzyl-3,5-trifluoromethyl-aniline 30.4 g of N-(2,2-dicyanovinyl)-aniline are dissolved in a solution of 5.61 g of potassium hydroxide in 100 ml of methanol. The methanol is distilled off and the residue is suspended in 150 ml of acetonitrile. To this suspension are added 12.6 g of benzyl chloride and the reaction mixture is stirred for 3 hours at 60°-70° C., then cooled and filtered clear. The acetonitrile is distilled off and the crude product is suspended in hot carbon tetrachloride and filtered hot. The above compound precipitates in yellow crystals from the filtrate after cooling. Melting point: 93°-96° C.

The following compounds were prepared by methods analogous to those described in the foregoing Examples:

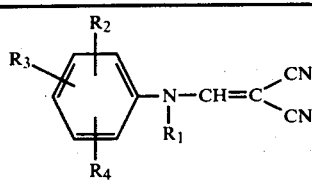

| Nr. | $R_1$ | $R_2$ | $R_3$ | $R_4$ | Physical data |
|---|---|---|---|---|---|
| 1 | H | H | H | H | 245° C. |
| 2 | H | H | 4-Cl | H | 273°-275° C. |
| 3 | H | 3-Cl | H | H | 193°-196° C. |
| 4 | H | 2-Cl | H | H | 144°-146° C. |
| 5 | H | 2-$CH_3$ | 4-Cl | H | 210°-214° C. |
| 6 | H | 2-Cl | H | 5-Cl | 182°-184° C. |

-continued

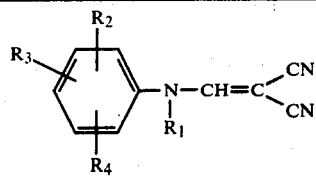

| Nr. | $R_1$ | $R_2$ | $R_3$ | $R_4$ | Physical data |
|---|---|---|---|---|---|
| 7 | H | 3-Cl | H | 5-Cl | 245°-250° C. |
| 8 | H | 2-Cl | 4-Cl | 5-Cl | 232°-235° C. |
| 9 | H | 3-$CF_3$ | 5-$CF_3$ | H | 233°-235° C. |
| 10 | H | H | —$NO_2$ | H | >215° C. |
| 11 | H | 3-$NO_2$ | H | H | 194°-196° C. |
| 12 | H | 2-$NO_2$ | H | H | 196°- C. |
| 13 | H | 3-$NO_2$ | 5-$NO_2$ | H | 220°-225° C. |
| 14 | H | 4-CN | H | H | >220° C. |
| 15 | H | 2-CN | H | H | 186° C. |
| 16 | H | 2-Br | 4-Br | H | 228°-231° C. |
| 17 | H | 3-$CF_3$ | H | H | 224°-226° C. |
| 18 | H | 3-Cl | 4-Cl | H | 260° C. |
| 19 | $CH_3$ | 3-$CF_3$ | 4-Cl | H | 94°-95° C. |
| 20 | —$CH_2$—$CH_3$ | 3-$NO_2$ | 5-$NO_2$ | H | |
| 21 | H | 2-$CH_3$ | 4-$NO_2$ | 5-Cl | 236°-238° C. |
| 22 | H | 4-$CH_3$ | 3-Cl | H | 220°-223° C. |
| 23 | H | 2-$CH_3$ | 5-$NO_2$ | H | 204°-208° C. |
| 24 | H | 2-$CH_3$ | 4-$NO_2$ | H | 220°-223° C. |
| 25 | H | 2-Cl | 3-Cl | H | 194°-198° C. |
| 26 | H | 2-$CH_3$ | 3-Cl | H | 184°-186° C. |
| 27 | H | 2-$CH_3$ | 4-Cl | H | 228°-231° C. |
| 28 | H | 2-$CH_3$ | 5-Cl | H | 220°-223° C. |
| 29 | H | 2-$CH_3$ | 6-Cl | H | 171°-173° C. |
| 30 | H | 4-$CH_3$ | 2-$NO_2$ | H | 216°-217° C. |
| 31 | H | 2-$CH_3$ | 3-$NO_2$ | H | 182°-185° C. |
| 32 | H | 3-$CH_3$ | 5-$NO_2$ | H | 241°-245° C. |
| 33 | H | 4-$CH_3$ | 3-$NO_2$ | H | 252°-253° C. |
| 34 | H | 6-CN | H | H | 263°-265° C. |

The following tests demonstrate the anthelmintic action of the anilinomethylenemalononitrile derivatives of the formula I.

1. Tests on mice attacked by *Nematospiroides dubius*

The active substances are administered in the form of a suspension with a stomach probe to white mice infected with *Nematospiroides dubius*. The active compounds are administered to each animal once daily on 3 successive days. The animals are then sacrificed on the 8th day after the start of the treatment and dissected.

Evaluation is made after dissection of the animals by counting the number of nematoda in the intestine. Untreated mice which were infected at the same time and in the same way were used as control.

The compositions are tolerated by the mice without any symptoms.

2. Tests on mice attacked by *Nippostrongylus brasiliensis*

The active substances are administered in the form of a suspension with a stomach probe to white mice infected with *Nippostrongylus brasiliensis*. Five animals are used for each test. The active compounds are administered once daily to each group of animals on successive days. The daily dose per animal is 100 mg of active compound/kg of body weight. The animals are then sacrificed on the 4th day after the start of the treatment and dissected. Evaluation is made after dissection of the test animals by comparing the number of parasites remaining in the intestine with an untreated control which had been infected in the same way at the same time.

3. Tests on mice attacked by *Hymenolepis nana*

The active substances are administered in the form of a suspension with a stomach probe to white mice which have been artificially infected with *Hymenolepis nana*. Five animals are used for each test. The active compounds are administered to each group of animals once daily on 3 successive days. The animals are sacrificed on the 4th day after the start of the treatment and dissected. Evaluation is made after dissection of the animals by comparing the number of tape worms present in the intestine with an untreated control which was infected at the same time in the same way.

4. Tests on rats infected with liver fluke (*Fasciola hepatica*)

White laboratory rats are infected with liver flukes (*Fasciola hepatica*). After expiry of the prepatent period, three infected rats per test are each treated once daily on 3 successive days with an active substance of the formula I in the form of a suspension using a stomach probe. Two weeks after administration of the active compound, the experimental animals are sacrificed and examined for the presence of liver flukes.

The results are reported in the following table:

| Active substance | Dose in mg/kg | Number of liver flukes | % age reduction compared with control |
|---|---|---|---|
| A | 3 × 5 | 0/0/3 | 85 |
| B | 3 × 10 | 0/0/0 | 100 |
| C | 3 × 30 | 0/0/0 | 100 |
| D | 3 × 300 | 0/0/0 | 100 |
| E | 3 × 10 | 0/0/0 | 100 |
| F | 3 × 10 | 0/0/0 | 100 |
| G | 3 × 3 | 0/0/0 | 100 |

Active substance (compounds)
A: N-(2,2-dicyanovinyl)-N-ethyl-3,5-bis-trifluoromethylaniline.
B: N-(2,2-dicyanovinyl)-3,5-bis-trifluoromethylaniline.
C: N-(2,2-dicyanovinyl)-2,4,5-trichloroaniline.
D: N-(2,2-dicyanovinyl)-3,5-dinitroaniline.
E: N-(2,2-dicyanovinyl)-N-propargyl-3,5-bis-trifluoromethylaniline.
F: N-(2,2-dicyanovinyl)-N-benzyl-3,5-bis-trifluoromethylaniline.
G: N-(2,2-dicyanovinyl)-2-methyl-4-nitro-5-chloroaniline.

The compositions of the present invention are used for combating helminths in domestic animals and productive livestock, such as cattle, sheep, goats, horses, pigs, cats, dogs and poultry. They can be administered to the animals in both individual and repeated doses. Depending on the species of animal, the individual doses are preferably administered in amounts between 0.5 and 100 mg/kg of body weight. A better action is often attained by protracted administration, or it is possible to manage with lower total doses. The active compounds, or mixtures containing them, can also be added to feeds and to troughs. The ready-prepared feeds contain the active compounds of the formula I preferably in a concentration of 0.005 to 0.1% by weight. The compositions can be administered to the animals perorally or in the form of solutions, emulsions, suspensions (drenches), powders, tablets, boluses and capsules. Conventional solid carriers are used for preparing these formulations, for example kaolin, talc, bentonite, common salt, calcium phosphate, cotton seed flour or liquids which do not react with the active compounds, such as oils and other solvents and diluents which are harmless to the animal organism. Provided the physical and toxicological properties of salutions or emulsions permit it, the active compounds can also be administered to the animals by subcutaneous injection.

If the anthelmintic compositions are in the form of feed concentrates, then suitable carriers are for example hay, production feeds, cereal feeds or protein concentrates. In addition to the active compounds, such feeds can contain additives, vitamins, antibiotics, chemotherapeutical agents or other pesticides, chiefly bacteriostats, fungistats, coccidiostats or also hormone preparations, substances having anabolic action or other substances which promote growth, enhance the quality of the flesh of slaughter animals, or are otherwise beneficial to the organism. They can also be combined with other anthelmintic agents, whereby their activity spectrum is broadened and adapted to given circumstances.

Examples of such substances are:

Nematocides: for example Absomal, Alcopar, Anthelcide, Ascaridol, Banmith II, Bephenium, Bradosol, Cambendazol, Calorophos, Chlorthion, Coumaphos, Cyanin, Destomycin, Diethylcarbamazin, Dichlorphen, DDVP, 1,4-di-(D-glyconyl)piperazine, Dithiazonin, Dow ET/70 Douco 132, Dymanthin HCl, Egressin, Gainex, Hexachlorophen, hexylresorcinol, Tonit, Levamisol, Meparin, methylene violet, ethyl-1-methyltridecylpiperazinium-4-carboxylate, Methyridin, Monopar, Marlene, Weguvon, Nematodin, Nemural, Nidanthel, Parbendazol, Parvex Phenothiazin, piperazine, polymethylenepiperazine, Promethanzin, Pyrantel, Pyranthiazin, pyrvinium embonate, Rametin, Ronnel, Santonin Shell 1808, Stilbazium, Tetramisol, Thenium, Thiabendazol, Thymolan, Vermella, Nebendazol;

Cestodicides: for example Acranil, Arecolin, Atebrin, Bithionol, dithionol oxide, Bunamidin, Cestodin, Cambendazol, dibutyl tin dilaurate, Dichlorophen, dioctyl tin dichloride, dioctyl tin dilaurate, Filixic acid, Hexachlorophen, Nidanthel, Terenol, Yomesan.

The anthelmintic compositions of the present invention are prepared in a manner known per se by homogeneously mixing and/or grinding active compounds of the formula I with suitable carriers, with or without the addition of dispersants or solvents which are inert to the active compounds.

The active substances may be processed to the following formulations:

Solid Formulations granules (coated granules, impregnated granules and homogeneous granules); water-dispersible active substance concentrates (wettable powders).

Liquid Formulations solutions, pastes, emulsions (especially ready for use emulsions).

For dusts and wettable powders, the granular size of the carriers is advantageously up to about 0.1 mm and for granules 10.500$\mu$ (0.01–0.5 mm).

In the solid formulations, the active substance concentrations are from 0.5 to 80%, and in the liquid formulations from 0.5 to 15%.

These mixtures can also contain additives which stabilise the active substance and/or nonionic, anionic and cationic substances which ensure for example an improved wettability (wetting agents) and dispersibility (dispersants).

Water-dispersible Powder Mixture

Composition:

25 parts of active substance of the formula I
3 parts of a mixture of polyoxyethylene-tall oil ester-urea
7 parts of polyvinyl pyrrolidone
31.5 parts of highly disperse silicic acid
33.5 parts of bolus alba.

The active substance is homogeneously mixed together with the polyoxyethylene tall oil ester-urea mixture and the polyvinyl pyrrolidone with the addition of about 30% of the silicic acid in a planetary mixer. The remainder of the silicic acid and the bolus alba are then added and the mixture is mixed in suitable mixers until homogeneous, and then ground to a particle size of less than 20μ in a disc mill.

What is claimed is:

1. A process for the control of parasitic helminths in warm blooded animals which comprises administering orally or subcutaneously to the animal an anthelmintically effective amount of a compound of the formula

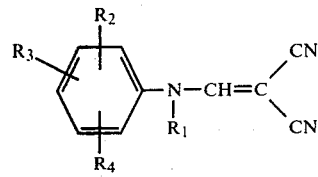

wherein
$R_1$ represents hydrogen, $C_1$-$C_6$ alkyl, the propargyl group or the benzyl radical,
$R_2$ represents hydrogen, $C_1$-$C_4$ alkyl, halogen, the trifluoromethyl group, the nitro group or the cyano group.
$R_3$ represents hydrogen, halogen, the trifluoromethyl group or the nitro group, and
$R_4$ represents hydrogen or halogen,
with the proviso that $R_1$ may only be the propargyl group or the benzyl radical if at least one of the symbols $R_2$ or $R_3$ represents the trifluoromethyl group.

2. The process of claim 1, wherein said compound $R_2$ and $R_3$, each independently of the other, represent hydrogen, halogen, methyl, trifluoromethyl or nitro.

3. The process of claim 1 for the control of parasitic trematoda.

4. The process of claim 3, wherein in said compound $R_2$ and $R_3$, each independently of the other, represent chlorine, methyl, trifluoro-methyl or nitro, and R represents hydrogen or chlorine.

* * * * *